United States Patent [19]
Lin

[11] Patent Number: 5,411,538
[45] Date of Patent: May 2, 1995

[54] IMPLANTABLE MEDICAL DEVICE WITH DETACHABLE BATTERY OR ELECTRONIC CIRCUIT

[75] Inventor: Jack H. Lin, Lake Jackson, Tex.

[73] Assignee: Intermedics, Inc., Angleton, Tex.

[21] Appl. No.: 146,904

[22] Filed: Nov. 1, 1993

[51] Int. Cl.⁶ ............................................. A61N 1/375
[52] U.S. Cl. ........................................ 607/33; 607/36
[58] Field of Search ........................ 607/33, 34, 36, 2

[56] References Cited

U.S. PATENT DOCUMENTS

| | | | |
|---|---|---|---|
| 4,119,103 | 10/1978 | Jirak | 607/9 |
| 4,787,389 | 11/1988 | Tarjan | 607/4 |
| 5,314,451 | 5/1994 | Mulier | 607/33 |

FOREIGN PATENT DOCUMENTS

| | | | |
|---|---|---|---|
| 0146388 | 2/1981 | Germany | 607/33 |
| 1274882 | 5/1972 | United Kingdom | 607/33 |

*Primary Examiner*—William E. Kamm
*Assistant Examiner*—Kennedy J. Schaetzle
*Attorney, Agent, or Firm*—John R. Merkling

[57] ABSTRACT

An implantable medical device, such as a pacemaker, cardioverter or defibrillator, having a detachable power source, so that either the power source or the electronic circuitry can be replaced. The device comprises an electronics package having a header for connection to leads coupled to the patient's heart and a battery connector comprising a header-like coupler. The device further comprises a battery pack having a second header-like coupler. The couplers mate together mechanically and are joined electrically by a separate pin. The pin has a coupling on both ends thereof so that one end can extend into the coupler of the electronics package and another end can extend into the coupler of the battery package. Alternatively, such a connector or pin, having a male configuration, could be provided on either the electronics coupler or the battery coupler with a corresponding female configuration on the other coupler.

12 Claims, 2 Drawing Sheets

IMPLANTABLE MEDICAL DEVICE WITH DETACHABLE BATTERY OR ELECTRONIC CIRCUIT

FIELD OF MY INVENTION

My invention is directed towards an implantable medical device such as a cardiac pacemaker or a cardioverter-defibrillator, and more specifically towards a cardiac stimulator having a replaceable battery or a replaceable electronic circuit.

BACKGROUND OF MY INVENTION

Electrically driven implantable devices are used principally as cardiac pacemakers, but they have also been considered for defibrillators; for heart assist, or drug infusion and dispensing systems; for bone growth and repair, pain suppression, or scoliosis treatment; for artificial vision, heart,or larynx; for stimulation of brain, nerves, muscle, gut or bladder; and for implanted sensors. For purposes of this disclosure, an implantable cardiac pacemaker/defibrillator is given as an example.

The basic pacemaker system consists of an electrode attached to the heart and connected by a flexible lead to a pulse generator. This generator is a combination of a power source and the microelectronics required for the pacemaker system to perform its intended function. A fixed rate pacemaker provides continuous pulses to the heart, irrespective of proper heart beating, while a demand inhibited pacemaker provides pulses only when the heart fails to deliver a natural pulse. Depending upon various sensed events, the pacemaker stimulates the right atrium, the right ventricle, or both chambers of the heart in succession. The pacemakers in current use incorporate circuits and antennae to communicate non-invasively with external instruments called programmers. Most of today's pacemakers are of the demand inhibited type, hermetically sealed, and programmable.

The longevity of pacemakers has been limited primarily by the capacity of their power sources. Early pacemakers were powered by primary zinc-mercuric oxide cells. Although this system was used for about 15 years, it did suffer from high self-discharge and hydrogen gas evolution. Because of gas evolution, the pacemaker could not be hermetically sealed, and had to be encapsulated in heavy epoxy. In 1970, the average life of the pulse generator was only 2 years, and 80 percent of explants were necessitated by failed batteries.

Consideration was given to many means of power generation and power storage. This included primary chemical batteries of all sorts, nuclear batteries, rechargeable batteries, and the separation of the stimulator system into two parts, with the power pack being outside the patient's body and transmitting pulses of energy to a passive implanted receiver and lead. Cardiac pacemakers based on rechargeable nickel-cadmium systems and rechargeable zinc-mercuric oxide systems were developed. Such pacemakers are described in prior art references, including U.S. Pat. Nos. 3,454,012; 3,824,129; 3,867,950; 3,888,260; and 4,014,346. The rechargeable pacemaker incorporated a charging circuit which was energized by electromagnetic induction, or other means. A replaceable battery has also been proposed by Kraska, eta/, U.S. Pat. No. 4,010,760.

Because the power supply or battery has generally been the limiting component in both implantable pacemakers and implantable defibrillators, it would be advantageous to provide a implantable cardiac stimulator which has a replaceable battery. Thus, instead of replacing the entire stimulator, only the battery need to be replaced as the power source nears its ends of life. Alternatively, a faulty or obsolete electronic circuit could be replaced or a circuit having different features could be substituted for the prior circuit. This should provide substantial economic benefits for the patient.

SUMMARY OF MY INVENTION

I have invented an implantable medical device, such as a pacemaker, cardioverter or defibrillator, having a detachable power source, so that either the power source or the electronic circuitry can be replaced. In my preferred embodiment, the stimulator comprises an electronics package having a header for connection to leads coupled to the patient's heart and a header-like coupler. The stimulator further comprises a battery pack having a second header-like coupler. The couplers mate together mechanically and are joined electrically by a separate pin. The pin has a configuration similar to the connection used for implantable leads, and preferably similar to the VS-1 standard for pacemaker leads, widely adopted in the pacemaker industry. The pin presents such a coupling on both ends thereof so that one end can extend into the coupler of the electronics package and another end can extend into the coupler of the battery package. Alternatively, such a connector or pin, having a male configuration, could be provided on either the electronics coupler or the battery coupler with a corresponding female configuration on the other coupler.

I will now describe a preferred embodiment of my invention with reference to the accompanying drawings.

DETAILED DESCRIPTION OF MY PREFERRED EMBODIMENT

Figure 1:
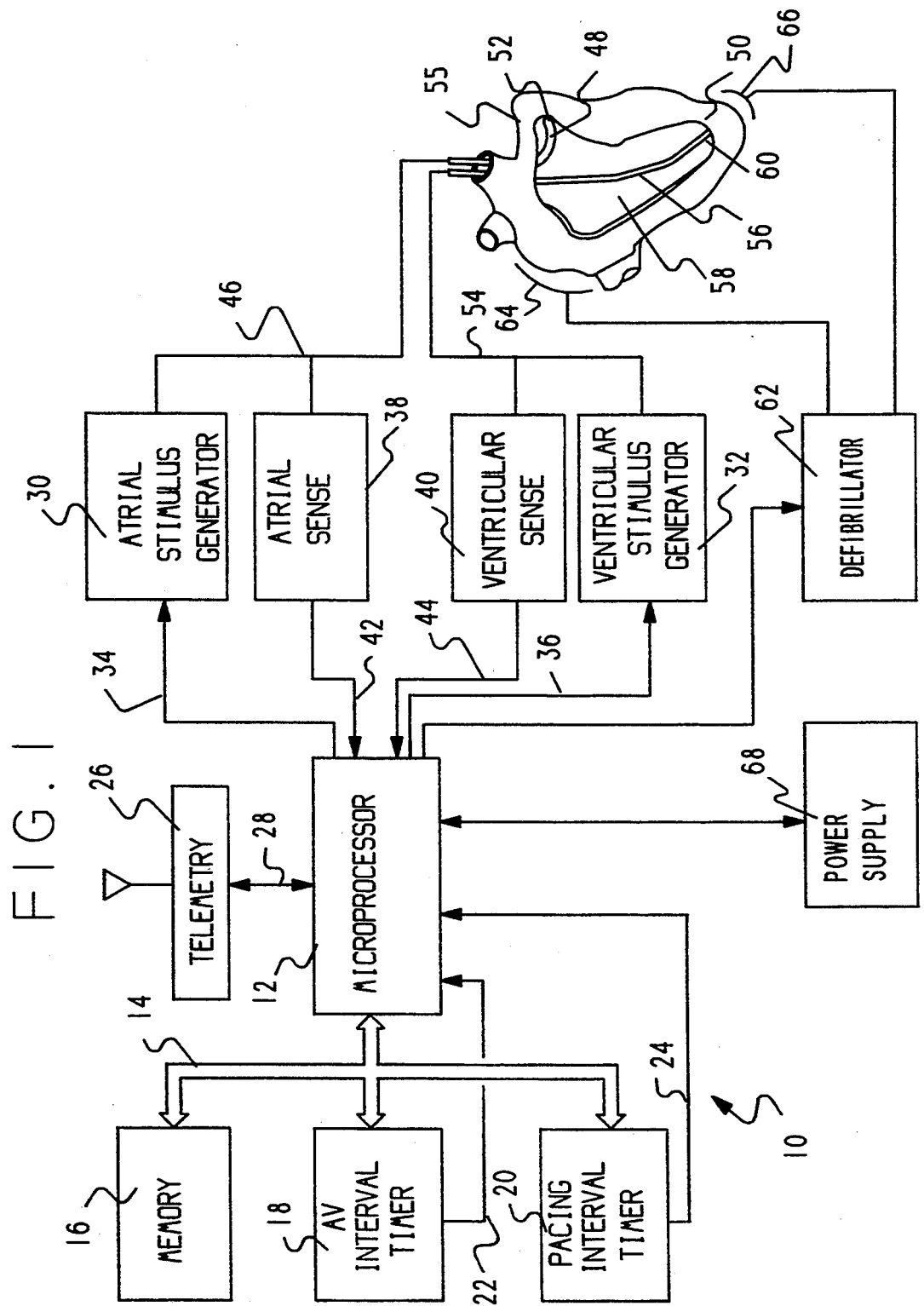
FIG. 1 is a block diagram of a pacemaker/defibrillator suitable for use in connection with my invention.

FIG. 1 is a block diagram illustrating an implantable pacemaker/defibrillator 10 according to my invention. A microprocessor 12 preferably provides pacemaker control and computational facilities. It will be appreciated that other forms of circuitry, such as analog or discrete digital circuitry can be used in place of microprocessor 12. However, a microprocessor is preferred for its miniature size and its flexibility, both of which are of critical importance in the implantable systems in which my invention will be used. A particularly energy efficient microprocessor which is designed specifically for such use is fully described in Gordon, et al., U.S. Pat. No. 4,404,972, which is also assigned to my assignee and the disclosure thereof is incorporated herein by reference.

The microprocessor 12 has input/output ports connected in a conventional manner via bi-directional bus 14 to memory 16, an A-V interval timer 18, and a pacing interval timer 20. In addition, the A-V interval timer 18 and pacing interval timer 20 each has an output connected individually to a corresponding input port of the microprocessor 12 by lines 22 and 24 respectively.

Memory 16 preferably includes both ROM and RAM. The microprocessor 12 may also contain additional ROM and RAM as described in the Gordon, et al. U.S. Pat. No. 4,404,972. The pacemaker operating routine is stored in ROM. The RAM stores various programmable parameters and variables.

The A-V and pacing interval timers 18 and 20 may be external to the microprocessor 50, as illustrated, or internal thereto, as described in the Gordon, et al. U.S. Pat. No. 4,404,972. The timers 18, 20 are suitable conventional up or down counters of the type that are initially loaded with a count value and count up to or down from the value and output a roll-over bit upon completing the programmed count. The initial count value is loaded into the timers 18, 20 on bus 14 and the respective roll-over bits are output to the microprocessor 12 on lines 22, 24.

The microprocessor 12 preferably also has an input-/output port connected to a telemetry interface 26 by line 28. The implanted pacemaker is thus able to receive pacing and rate control parameters from an external programmer and send data to an external receiver if desired. Many suitable telemetry systems are known to those skilled in the art. One such system and encoding arrangement is described in Calfee, et al. U.S. Pat. No. 4,539,992 which is also assigned to my assignee. That description is incorporated herein by reference.

The microprocessor 12 output ports are connected to inputs of an atrial stimulus pulse generator 30 and a ventricle stimulus pulse generator 32 by control lines 34 and 36 respectively. The microprocessor 12 transmits pulse parameter data, such as amplitude and width, as well as enable/disable and pulse initiation codes to the generators 30, 32 on the respective control lines.

The microprocessor 12 also has input ports connected to outputs of an atrial sense amplifier 38 and a ventricular sense amplifier 40 by lines 42 and 44 respectively. The atrial and ventricular sense amplifiers 38, 40 detect occurrences of P-waves and R-waves respectively. The atrial sense amplifier 30 outputs a signal on line 42 to the microprocessor 12 when it detects a P-wave. This signal is latched to the microprocessor 12 input port by a conventional latch (not shown). The ventricular sense amplifier 40 outputs a signal on line 44 to the microprocessor 12 when it detects an R-wave. This signal is also latched to the microprocessor 12 input port by a conventional latch (not shown).

The input of the atrial sense amplifier 38 and the output of the atrial stimulus pulse generator 30 are connected to a first conductor 46, which passes through a conventional first lead 48. Lead 48 is inserted into a patient's heart 50 intravenously or in any other suitable manner. The lead 48 has an electrically conductive pacing/sensing tip 52 at its distal end which is electrically connected to the conductor 46. The pacing/sensing tip 52 is preferably lodged in the right atrium 54.

The input of the ventricular sense amplifier 40 and the output of the ventricular stimulus pulse generator 32 are connected to a second conductor 54. The second conductor 54 passes through a conventional second lead 56 which is inserted intravenously or otherwise in the right ventricle 58 of the heart 50. The second lead 56 has an electrically conductive pacing/sensing tip 60 at its distal end. The pacing/sensing tip 60 is electrically connected to the conductor 54. The pacing/sensing tip 60 is preferably lodged on the wall of the right ventricle 58.

The conductors 46, 54 conduct the stimulus pulses generated by the atrial and ventricular stimulus pulse generators 30, 32 respectively, to the pacing/sensing tips 52, 60. The pacing/sensing tips 52, 60 and corresponding conductors 46, 54 also conduct cardiac electrical signals sensed in the right atrium and right ventricle to the atrial and ventricular amplifiers, 38, 40 respectively. The sense amplifiers 38, 40 enhance the electrical signals. In the preferred embodiment of my invention, the amplifiers 38, 40, have an automatic gain control feature, as described in U.S. Pat. No. 4,903,699 to Baker, et al. That application is assigned to the same assignee as my present invention, and the disclosure thereof is incorporated herein by reference.

The implantable cardiac stimulator 10 may also have a defibrillator circuit 62. If fibrillation is detected through the atrial or ventricular sense amplifiers 38, 40 a high energy shock can be delivered through defibrillation electrodes 64, 66. Although patch-type electrodes 64, 66 are suggested, endocardial electrodes for defibrillation are also known.

Figure 2:
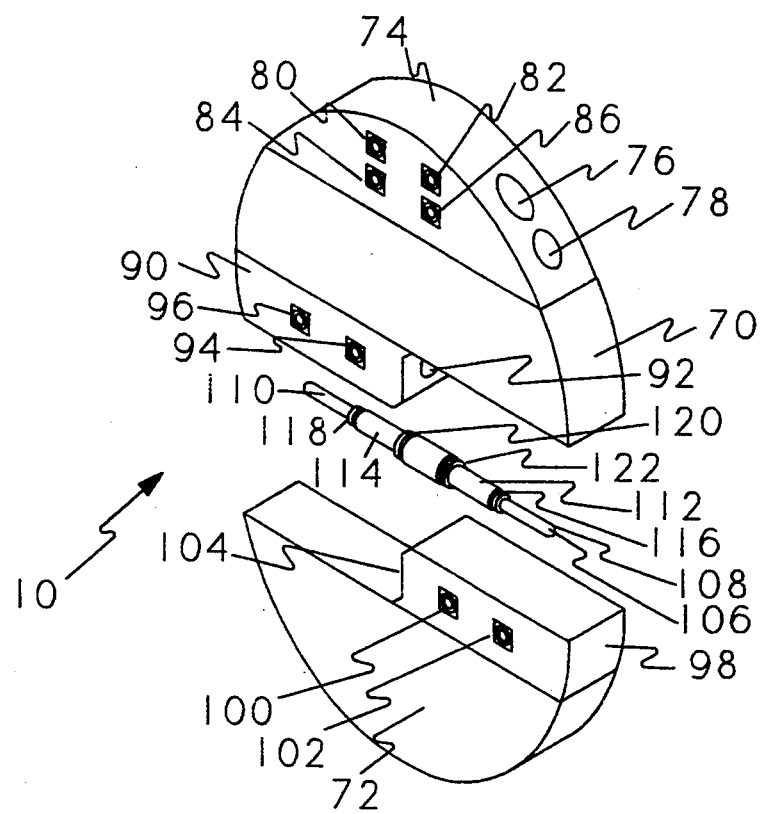
FIG. 2 is an exploded perspective view for the pacemaker/defibrillator according to my invention.
Figure 3:
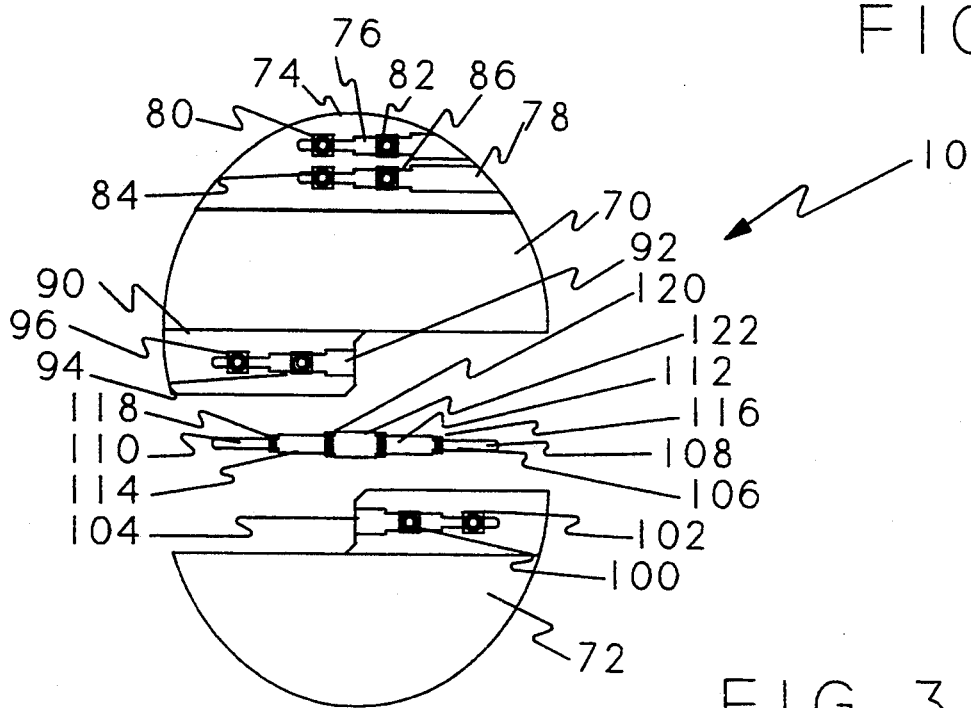
FIG. 3 is a front plan view of the pacemaker/defibrillator of FIG. 2.

The implantable cardiac stimulator 10 with detachable battery is shown in an exploded perspective view in FIG. 2 and in exploded plan view in FIG. 3. The stimulator 10 comprises an electronics package 70 which contains the microprocessor 12 and other electronic functions described above, with the exception of the power supply 68. The power supply 68 preferably comprises batteries contained in a battery package 72. The electronics package 70 has a header 74 provided with a plurality of female lead receptacles 76, 78. These receptacles preferably conform to the VS-1 voluntary industry standard for lead connections. Each of lead receptacles 76, 78 has associated with it connectors 80 and 82 and 84 and 86 respectively. The connectors 80, 82, 84, 86 secure leads in the receptacles 76, 78 with cap screws. Alternatively, the leads could be secured with a sidelock (TM) connector such as that disclosed by Frey, et al., in U.S. Pat. No. 4,860,750. Whenever such cap-screw type connectors are mentioned herein, a sidelock (TM) connector or other fastener could be substituted.

Opposite the header 74 on the electronics package 70 there is a first header-like coupler 90. The coupler 90 comprises a female receptacle 92 with two connectors 94, 96. The first coupler 90 mechanically interfaces with a second header-like coupler 98 on the battery package 72. The second coupler 98 also has two connectors 100 and 102 and a female receptacle 104. Both the receptacles 92 and 104 preferably conform with the VS-1 voluntary standard mentioned above. A special pin 106 is provided to couple both couplers 90, 98. This pin has conductors for the anode and cathode of both the battery and electronics couplers, each separated by integral o-rings. Thus, there is a battery cathode 108 and a corresponding electronics cathode 110 in electrical communication with the battery cathode 108. Similarly, there is a battery anode 112 and a corresponding electronics anode 114, in electrical communication with the battery anode 112. 0-ring seals 116 are provided between the battery anode 112 and cathode 108. Similarly, o-ring seals 118 are provided between the electronics anode 114 and cathode 110. Finally, additional o-ring seals 120, 122, between the electronics anode 114 from the battery anode 112 (and also, therefore, between the two cathodes which are beyond the anodes) are used to prevent moisture from migrating into the receptacles 92 and 104 and inducing any leakage.

My invention may be embodied in other forms without departing from the teachings thereof. The foregoing description is intended, therefore to be illustrative, and not restrictive. The scope of my invention is defined by the following claims, and all equivalents are intended to be included therein.

I claim as my invention:

1. An implantable medical device comprising electronic circuit means;
first container means enclosing said electronic circuit means battery means;
second container means enclosing said battery means; and
means for detachably coupling said electronic circuit means and said battery means, said coupling means comprising
a pin having
a first end with a first anode and a first cathode and ring means between said first anode and said first cathode for inhibiting passage of body fluids, and
a second end with a second anode and a second cathode, spaced apart from said first anode and said first cathode, and ring means between said second anode and said second cathode for inhibiting passage of body fluids,
a first receptacle for receiving first end of said pin, and
a second receptacle for receiving said second end of said pin.

2. The medical device according to claim 1 further comprising a cardiac pacemaker.

3. The medical device according to claim 1 further comprising a defibrillator.

4. The medical device according to claim 1 wherein said second anode and second cathode are spaced apart from each other on said pin and said pin further comprises a ring means between said second anode and second cathode for sealing fluids out of said second receptacle.

5. The medical device according to claim 4 further comprising a cardiac pacemaker.

6. The medical device according to claim 4 further comprising a defibrillator.

7. The medical device according to claim 4 wherein said pin further comprises at least one ring means between said first anode and cathode and said second anode and cathode for sealing fluids out of said receptacles.

8. The medical device according to claim 7 further comprising a cardiac pacemaker.

9. The medical device according to claim 7 further comprising a defibrillator.

10. The medical device according to claim 7 further comprising first coupler means on said first container means, said first coupler means including said first receptacle, and second coupler means on said second container means, said first coupler means including said second receptacle, said first and second coupler means being configured to contact one another when said pin is assembled in said first and second receptacles.

11. The medical device according to claim 10 further comprising a cardiac pacemaker.

12. The medical device according to claim 10 further comprising a defibrillator.

* * * * *